US008066030B2

(12) United States Patent
Schelhas et al.

(10) Patent No.: US 8,066,030 B2
(45) Date of Patent: Nov. 29, 2011

(54) FUEL CONVEYING DEVICE

(75) Inventors: Peter Schelhas, Stuttgart (DE); Andreas Herforth, Leonberg (DE); Zdenek Liner, Tyn Nad Vltavou (CZ); Michael Dufek, Ceske Budejovice (CZ); David Krenovsky, Ceske Budejovice (CZ)

(73) Assignee: Robert Bosch GmbH, Stuttgart (DE)

( * ) Notice: Subject to any disclaimer, the term of this patent is extended or adjusted under 35 U.S.C. 154(b) by 604 days.

(21) Appl. No.: 12/088,287

(22) PCT Filed: Aug. 16, 2006

(86) PCT No.: PCT/EP2006/065347

§ 371 (c)(1),
(2), (4) Date: Mar. 27, 2008

(87) PCT Pub. No.: WO2007/045519

PCT Pub. Date: Apr. 26, 2007

(65) Prior Publication Data

US 2008/0251052 A1 Oct. 16, 2008

(30) Foreign Application Priority Data

Oct. 19, 2005 (DE) ........................ 10 2005 049 982

(51) Int. Cl.

| | |
|---|---|
| ***F16K 17/26*** | (2006.01) |
| ***E03B 5/00*** | (2006.01) |
| ***A61M 1/00*** | (2006.01) |
| ***B01D 21/30*** | (2006.01) |
| ***F02M 37/00*** | (2006.01) |
| ***B05B 1/30*** | (2006.01) |

(52) U.S. Cl. ................ 137/565.15; 137/493; 137/493.6; 137/493.8; 137/565.13; 123/511; 239/570; 239/571

(58) Field of Classification Search .................... 239/91, 239/349, 354, 570, 571, 584; 123/511, 512, 123/514, 516, 461; 137/247.15, 467, 469, 137/493.8, 493, 493.6, 565.13, 565.15
See application file for complete search history.

(56) References Cited

U.S. PATENT DOCUMENTS

| | | | | |
|---|---|---|---|---|
| 3,131,708 A * | 5/1964 | Knight | 137/113 |
| 3,913,601 A * | 10/1975 | Hanson | 137/39 |
| 5,477,829 A * | 12/1995 | Hassinger et al. | 123/467 |
| 5,762,101 A * | 6/1998 | Burke et al. | 137/469 |
| 6,837,219 B2 * | 1/2005 | York et al. | 123/457 |
| 2004/0149266 A1 | 8/2004 | York et al. | |
| 2008/0095642 A1 * | 4/2008 | Schelhas et al. | 417/189 |

FOREIGN PATENT DOCUMENTS

| | | |
|---|---|---|
| DE | 195 27 134 A1 | 3/1996 |
| DE | 101 35 171 A1 | 2/2002 |

* cited by examiner

*Primary Examiner* — Dinh Nguyen
*Assistant Examiner* — Ryan Reis
(74) *Attorney, Agent, or Firm* — Ronald E. Greigg

(57) ABSTRACT

Disclosed is a fuel conveying device including a valve housing in which a pressure release valve and a non-return valve are arranged parallel to one another, the pressure release valve having a first inlet, which downstream of a valve seat opens into a valve chamber in which a valve body is movably arranged and which is in fluid connection with a second inlet for the non-return valve via a first outlet. The device improves the control response of the pressure release valve by providing the first outlet at the periphery of the valve chamber and in the axial direction with respect to a valve axis such that when the pressure release valve is open the flow from the valve chamber into the second inlet is a substantially radial flow.

20 Claims, 3 Drawing Sheets

FUEL CONVEYING DEVICE

CROSS-REFERENCE TO RELATED APPLICATION

This application is a 35 USC 371 application of PCT/EP 2006/065347 filed on Aug. 16, 2006.

BACKGROUND OF THE INVENTION

1. Field of the Invention

The invention is directed to an improved fuel conveying device of the type used, for example, for supplying fuel to an internal combustion engine.

2. Description of the Prior Art

A fuel conveying device known from DE 195 27 134 A1 is equipped with a valve housing in which a pressure relief valve and a check valve are situated in parallel with each other; the pressure relief valve has a first inlet that, downstream of a valve seat, opens into a valve chamber in which a valve member is movably arranged and which, via a first outlet, is flow connected to a second inlet for the check valve. It is disadvantageous that the first outlet is situated in the valve chamber in a way that produces an axial outflow from the valve chamber of the pressure relief valve. The axial outflow exerts only a comparatively slight impulse force on the valve member, which therefore executes only a comparatively small opening stroke for a given volumetric flow. This results in a control response that is less than optimal.

SUMMARY AND ADVANTAGES OF THE INVENTION

The fuel conveying device according to the present invention has the advantage over the prior art that it improves the regulating behavior of the pressure relief valve in a simple way in that the first outlet is provided at the periphery of the valve chamber and is arranged in the axial direction such that when the pressure relief valve is open, an essentially radial outflow occurs from the valve chamber into the second inlet.

Advantageous modifications and improvements of the device are disclosed. It is particularly advantageous if the pressure relief valve and the check valve are arranged offset from each other in the axial direction so that the first outlet of the pressure relief valve feeds into the second inlet of the check valve in the radial direction. This achieves a radial outflow into the second inlet of the check valve.

It is also advantageous if the valve housing has a first recess for insertion of the pressure relief valve and a second recess that constitutes the second inlet for the check valve since this embodiment is particularly inexpensive to manufacture. The first recess and second recess are separated from each other by a wall.

It is particularly advantageous if the valve housing has two cylindrical sections, with one of the recesses provided in each section, since this embodiment is particularly space-saving.

It is also advantageous if the pressure relief valve has a separate housing on which the valve seat is embodied and in which the valve chamber with the valve member is provided since this simplifies the valve housing and makes it less expensive to manufacture.

It is also advantageous if the housing of the pressure relief valve is situated directly on the fuel conveying device and is attached to it.

BRIEF DESCRIPTION OF THE DRAWINGS

An exemplary embodiment of the invention is explained in greater detail herein below, with reference to the drawings, in which.

DESCRIPTION OF THE PREFERRED EMBODIMENT

Figure 1:
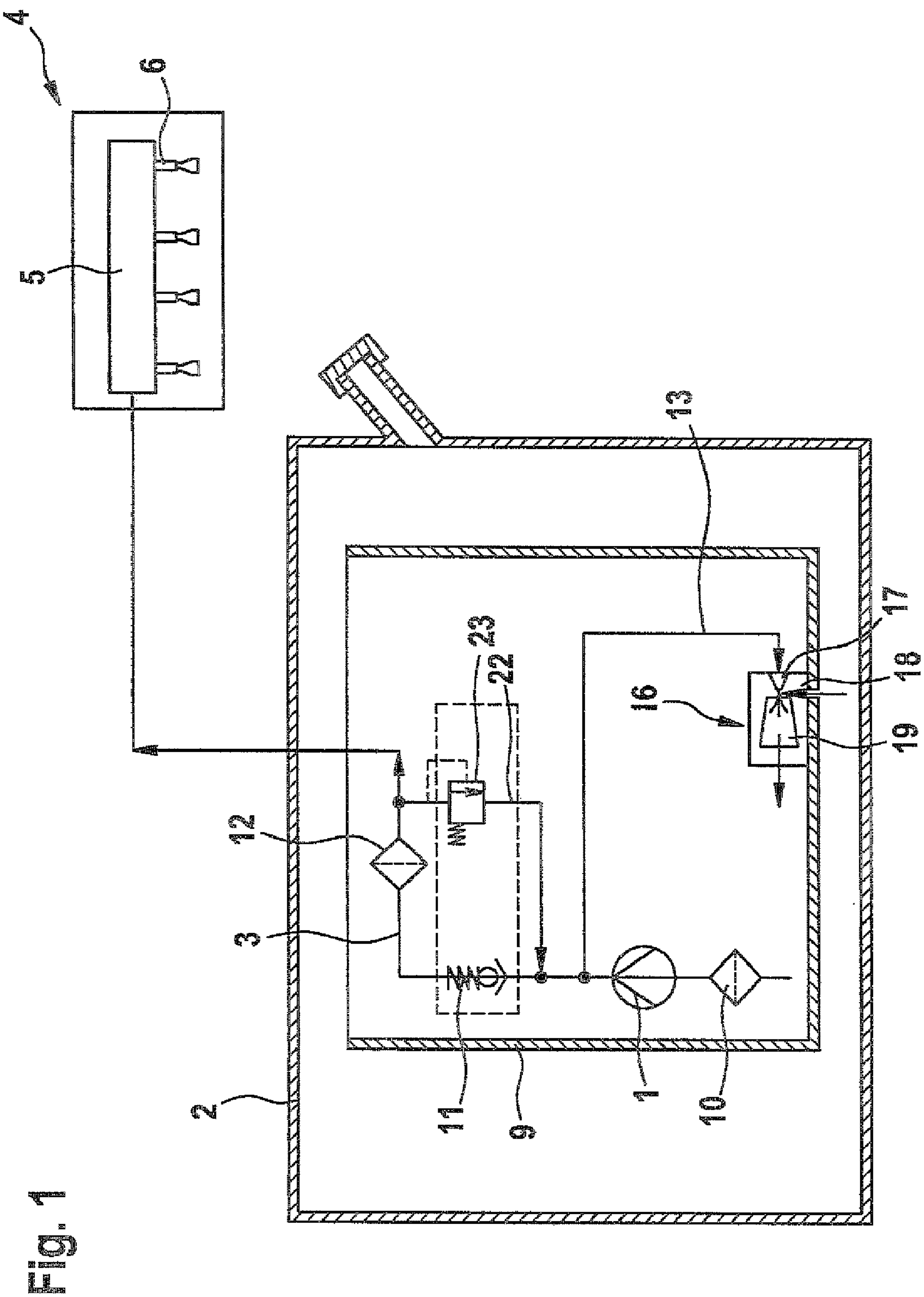
FIG. 1 is a schematic depiction of a conventional fuel conveying device.

FIG. 1 is a schematic depiction of a fuel conveying device suitable to convey fuel, although the device is expressly also able to convey other fluids.

The device has a delivery unit 1 that draws fuel at least indirectly from a tank 2 and conveys it at an elevated pressure via a pressure line 3 to an internal combustion engine 4, for example by supplying it to a fuel distributor 5. The fuel distributor 5 is flow connected to injection valves 6 that inject the fuel into a combustion chamber, not shown, of the internal combustion engine 4.

The delivery unit 1 is situated, for example, in the tank 2 and is provided, for example, inside a storage receptacle 9 therein. The deliver unit 1 draws fuel from this storage receptacle 9, for example via a preliminary filter 10, and delivers it to the internal combustion engine 4 via the pressure line 3. The preliminary filter 10 protects the device downstream of the filter 10 from coarse dirt particles contained in the fuel. A check valve 11, for example, is situated in the pressure line 3 to prevent fuel downstream of the check valve 11 from flowing back upstream of the check valve 11. In addition, a main filter 12 that filters out fine dirt particles from the fuel is situated, for example, in the pressure line 3 downstream of the check valve 11. Downstream of the delivery unit 1 and upstream of the check valve 11, a drive line 13 branches off from the pressure line 3 and leads at least indirectly back into the storage receptacle 9. The volumetric flow of the drive line 13 drives a so-called suction jet pump 16, for example, which conveys fuel from the tank 2 into the storage receptacle 9. The for example cup-shaped storage receptacle 9 stores enough fuel to assure the delivery unit 1 of being able to supply fuel to the internal combustion engine 4 even during cornering and the accompanying sloshing movements of the fuel in the tank 2.

The suction jet pump 16 must be designed so that the storage receptacle 9 remains filled regardless of the level of fuel in the tank 2 and does not run dry. As is known, the suction jet pump 20 has a throttle element, for example a nozzle 17, via which the fuel of the drive line 13 travels into a suction chamber 18 flow connected to the tank 2. The motive jet coming from the nozzle 17 and traveling into the suction chamber 18 entrains fuel from the suction chamber 18 so that the fuel of the motive jet and the entrained fuel travel together in a known fashion into the storage receptacle 9 via a mixing conduit 19.

Downstream of the check valve 11 and, for example, downstream of the main filter 12, a return line 22 that contains a pressure relief valve 23 branches off from the pressure line 3 and leads back into the pressure line 3 upstream of the check valve 11.

According to the invention, the check valve 11 and the pressure relief valve 23 are accommodated in a combined valve housing 24.

Figure 2:
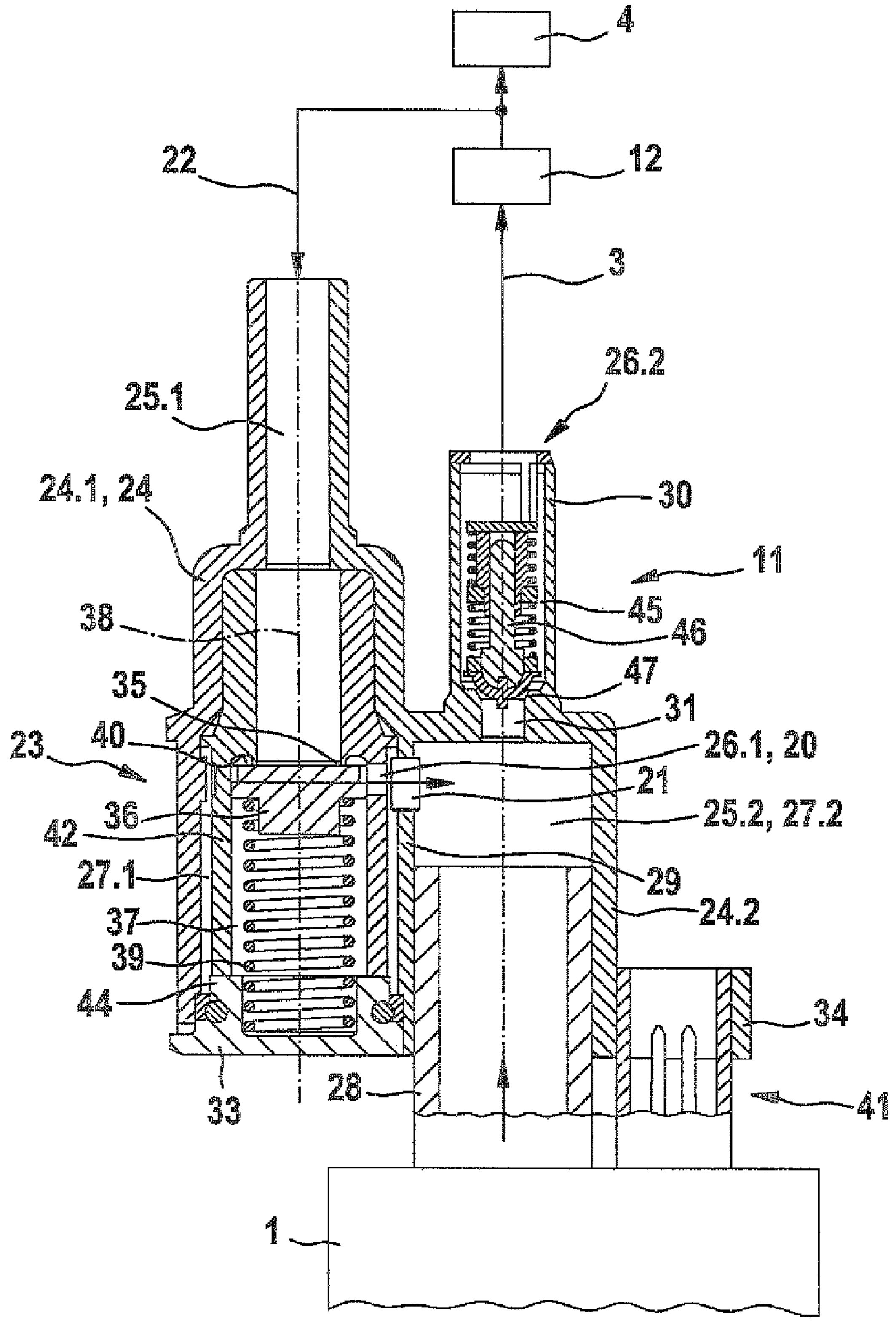
FIG. 2 is a simplified sectional view of a valve housing according to the invention, equipped with a check valve and a parallel-connected pressure relief valve.

FIG. 2 shows a valve housing according to the invention, equipped with a check valve and a parallel-connected pressure relief valve.

In the device according to FIG. 2, parts that remain the same or function in the same fashion as those in the device according to FIG. 1 have been labeled with the same reference numerals.

The valve housing 24 has a first inlet 25.1 and first outlet 26.1 for the pressure relief valve 23 and a second inlet 25.2 and second outlet 26.2 for the check valve 11. The first outlet 26.1 of the pressure relief valve 23 feeds directly into the second inlet 25.2 of the check valve 11.

The valve housing 24 has two separate, for example cup-shaped, recesses 27.1, 27.2 that are separated from each other by a wall 29. A first recess 27.1 accommodates the pressure relief valve 23 and a second recess 27.2 constitutes the second inlet 25.2 for the check valve 11. The second recess 27.2 of the valve housing 24 can be slid onto an outlet fitting 28 of the delivery unit 1, thus tightly sealing the flow connection between the outlet fitting 28 of the delivery unit 1 and the valve housing 24. In this way, the valve housing 24 is situated directly on the delivery unit 1. A mount 34 situated on the valve housing 24 attaches the valve housing 24 to the delivery unit 1 in a form-locked and/or non-positive and/or integrally joined fashion. For example, the mount is attached to an electrical plug 41 of the delivery unit in a form-locked and/or non-positive fashion.

The recesses 27.1, 27.2 are provided, for example, on two cylindrical housing sections of the valve housing 24, with the first recess 27.1 being provided in a first cylindrical section 24.1 and the second recess 27.2 being provided in a second cylindrical section 24.2. The two cylindrical sections 24.1, 24.2 of the valve housing 24 are integrally joined to each other. The first cylindrical section 24.1 protrudes beyond the second cylindrical section 24.2 in its longitudinal direction. The first inlet 25.1 is situated at an end of the first cylindrical section 24.1 and the second inlet 25.2 is situated at an end of the second cylindrical section 24.2 oriented away from the first inlet 25.1.

The first recess 27.1 is closed by means of a cover 33 that has a shoulder 44, for example, protruding into the first recess 27.1. In this way, the pressure relief valve 23 in the first recess 27.1 is tightly sealed in relation to the atmosphere.

At an end of the second cylindrical section 24.2 oriented away from the second inlet 25.2, there is a fitting 30 in which the check valve 11 is provided. The second inlet 25.2 feeds via a connecting conduit 31 into an additional valve chamber 45 of the check valve 11, which valve chamber 45 is provided inside the fitting 30. An additional valve member 46 is movably arranged in the additional valve chamber 45 and cooperates with all additional valve seat 47.

The pressure relief valve 23 contained in the first recess 27.1 has a valve member 36 that cooperates with the valve seat 35 and is situated so that it can move in the axial direction with respect to a valve axis 38. A valve spring 39 presses the valve member 36 toward the valve seat 35. The valve seat 35 is embodied, for example, in the form of a flat seat and cooperates with a flat end of the for example cylindrical valve member 36. For example, the valve seat 35 is embodied in the form of a raised annular surface on an end wall 40 of the valve chamber 37.

For example, the pressure relief valve 23 has its own separate housing 42 on which the valve seat 35 is embodied and in which the valve chamber 37, the valve member 36, and valve spring 39 are provided.

According to present invention, the first outlet 26.1 of the pressure relief valve 23 is provided at the periphery of the valve chamber 37 and is oriented in the radial direction with respect to the valve axis 38 so that when the pressure relief valve 23 is open, an essentially radial outflow is produced from the valve chamber 37 into the first outlet 25.1 and into the second inlet 25.2. The first outlet 26.1 of the pressure relief valve 23 is situated close to the valve seat 35 in the axial direction with respect to the valve axis 38, for example in the same axial position as it. For example, the first outlet 26.1 extends through a first opening 20 at the periphery of the housing 42 of the pressure relief valve 23 and through a second opening 21 in the wall 29 between the recesses 27.1, 27.2. The first opening 20 and the second opening 21 are aligned with each other. The pressure relief valve 23 and the check valve 11 are offset from each other in the axial direction with respect to the valve axis 38 so that the first outlet 26.1 of the pressure relief valve 23 feeds into the second inlet 25.2 in the radial direction with respect to the valve axis 38.

If the pressure in the return line 22 exceeds a value predetermined by the spring force of the valve spring 39, then the valve member 36 lifts away from the valve seat 35, thus opening the pressure relief valve 23. After the pressure relief valve 23 opens, fuel flows through the axial first inlet 25.1, into the valve chamber 37 in the axial direction through a gap produced between the valve seat 35 and the valve member 36, and exits this valve chamber 37 in the radial direction via the first outlet 26.1. The flat seat permits a particularly favorable outflow in the radial direction.

An impulse force due to the deflection of the fluid from the axial direction into the radial direction acts on the valve member 36, causing it to move in the direction away from the valve seat 35, counter to the spring force of the valve spring 39 until a force equilibrium with the spring force is achieved. The impulse force of the flow increases as the flow through the pressure relief valve 23 increases. The spring force of the valve spring 39 increases in linear fashion as the stroke of the valve member 36 increases. An influx through the first inlet 25.1 into the valve chamber 37 in the axial direction with an outflow from the valve chamber 37 in the radial direction according to the invention maximizes the impulse force that the fuel exerts on the valve member 36. The prior art, with both the inflow and outflow oriented in the axial direction, however, results in a weaker impulse force acting on the valve member 36.

The impulse force works in opposition to the spring force. Ideally, the impulse force, which increases with increasing flow, compensates for the spring force, which increases with the stroke movement of the valve member 36. As a result, the regulating pressure is kept as independent of the flow as possible.

The greater the impulse force acting on the valve member 36, the larger the opening stroke executed by the valve member 36 and therefore the lower the overall pressure loss of the pressure relief valve 23 for a given flow.

The overall pressure loss of the pressure relief valve 23 essentially results from the pressure loss in the gap between the valve seat 35 and the valve member 36. The pressure loss at this gap decreases as the stroke of the valve member 36 increases.

In the prior art with the axial outflow, however, an additional pressure loss occurs with the axial flow around the valve member 36. This additional pressure loss in the prior at increases as the flow increases. The additional pressure loss that occurs in the prior art does not occur in the pressure relief valve 23 according to the invention since instead of an axial flow around the valve member 36, a radial outflow occurs.

The elimination of the additional pressure loss achieves a better regulating behavior of the pressure relief valve 23 in comparison to the prior art since the overall pressure loss changes less markedly when slight changes in the flow occur.

In this way, the pressure in the return line 22 and the pressure line 3 are kept virtually constant.

Figure 3:
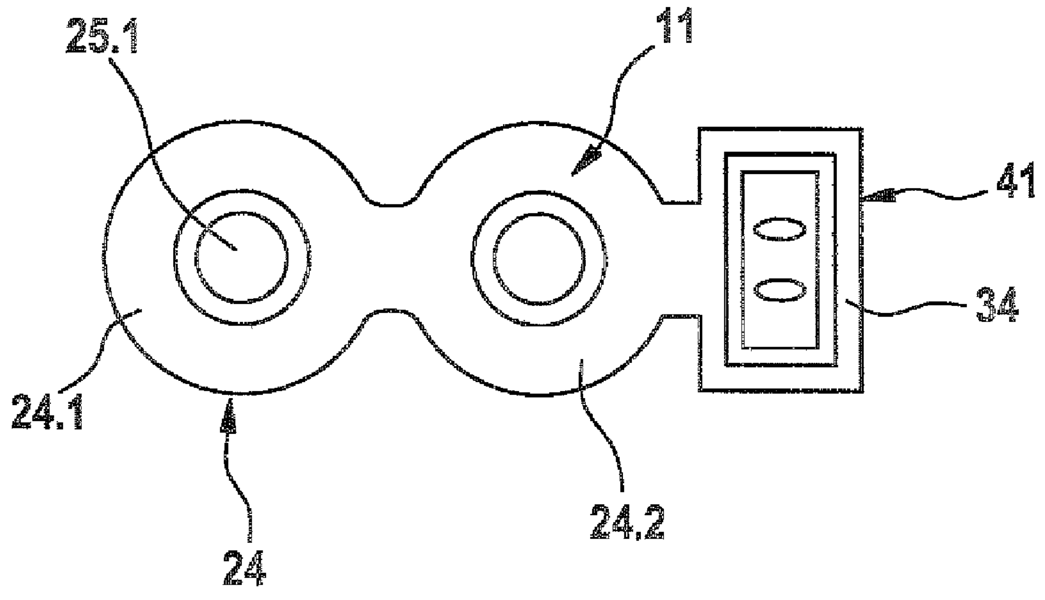
FIG. 3 is a top view of the valve housing.

FIG. 3 is a top view of the valve housing.

In the device according to FIG. 3, parts that remain the same or function in the same fashion as those in the device according to FIG. 1 and FIG. 2 have been labeled with the same reference numerals.

The foregoing relates to a preferred exemplary embodiment of the invention, it being understood that other variants and embodiments thereof are possible within the spirit and scope of the invention, the latter being defined by the appended claims.

The invention claimed is:

1. In a fuel conveying device equipped with a valve housing in which a pressure relief valve and a check valve are situated in parallel with each other;

wherein the pressure relief valve has a first inlet that, downstream of a valve seat, opens into a valve chamber in which a valve member is movably arranged and which, via a first outlet, is flow connected to a second inlet for the check valve, wherein the first outlet is provided at a periphery of the valve chamber and is arranged in an axial direction with respect to a valve axis such that when the pressure relief valve is open, an essentially radial outflow occurs from the valve chamber into the second inlet, wherein the pressure relief valve and the check valve are arranged offset from each other in the axial direction so that the first outlet of the pressure relief valve feeds into the second inlet of the check valve in the radial direction, and the first outlet of the pressure relief valve is situated close to its valve seat in the axial direction with respect to the valve axis in such a way that no axial flow around the pressure relief valve member occurs when the pressure relief valve is open, wherein the check valve is located within a pressure line through which fuel is conveyed from a point within the pressure line that is upstream of said check valve to a point within the pressure line that is downstream of said check valve, and wherein the pressure relief valve receives fuel from a point within the pressure line that is downstream of said check valve and allows it to flow back to a point within the pressure line that is upstream of said check valve.

2. The device according to claim 1, wherein the valve housing comprises a first recess for insertion of the pressure relief valve and a second recess that constitutes the second inlet for the check valve.

3. The device according to claim 2, wherein the first recess and second recess are separated from each other by a wall.

4. The device according to claim 2, wherein the recesses are each provided in cylindrical housing sections.

5. The device according to claim 3, wherein the recesses are each provided in cylindrical housing sections.

6. The device according to claim 2, wherein the first recess is closed by a cover.

7. The device according to claim 3, wherein the first recess is closed by a cover.

8. The device according to claim 4, wherein the first recess is closed by a cover.

9. The device according to claim 4, wherein the cylindrical housing sections are integrally joined to each other.

10. The device according to claim 1, wherein the pressure relief valve comprises a separate housing on which the valve seat is embodied and in which the valve chamber with the valve member is provided.

11. The device according to claim 2, wherein the pressure relief valve comprises a separate housing on which the valve seat is embodied and in which the valve chamber with the valve member is provided.

12. The device according to claim 1, wherein the valve seat is embodied as a flat seat.

13. The device according to claim 1, further comprising a valve spring pressing the valve member toward the valve seat.

14. The device according to claim 13, wherein the first outlet of the pressure relief valve is closer to the first inlet in the axial direction than the spring.

15. The device according to claim 13, wherein the first outlet of the pressure relief valve is situated close to its valve seat in the axial direction with respect to the valve axis in such a way that no axial flow around the spring occurs when the pressure relief valve is open.

16. The device according to claim 1, wherein the first outlet of the pressure relief valve is located adjacent to the pressure relief valve member.

17. The device according to claim 1, wherein the first outlet of the pressure relief valve is radially aligned with the pressure relief valve member.

18. The device according to claim 1, wherein the check valve prevents fuel downstream of the check valve from flowing back upstream through the pressure line.

19. The device according to claim 1, wherein said outflow is essentially radial throughout an entire distance from the valve chamber to the second inlet.

20. The device according to claim 1, wherein the second inlet forms an indentation into which an outlet fitting of a delivery unit is inserted, which delivery unit delivers fuel to an internal combustion engine via the check valve.

* * * * *